United States Patent [19]
Roby et al.

[11] Patent Number: 5,914,387
[45] Date of Patent: Jun. 22, 1999

[54] POLYESTERAMIDES WITH AMINO ACID-DERIVED GROUPS ALTERNATING WITH ALPHA-HYDROXYACID-DERIVED GROUPS AND SURGICAL ARTICLES MADE THEREFROM

[75] Inventors: Mark S. Roby, Killingworth; Ying Jiang, North Haven, both of Conn.

[73] Assignee: United States Surgical Corporation, Norwalk, Conn.

[21] Appl. No.: 09/014,802

[22] Filed: Jan. 28, 1998

Related U.S. Application Data

[60] Provisional application No. 60/036,542, Jan. 28, 1997.

[51] Int. Cl.⁶ .................................................... C08G 69/44
[52] U.S. Cl. ......................... 528/310; 528/170; 528/322; 528/323; 528/327; 528/354; 528/355; 528/361; 525/411; 525/415; 525/417; 606/139; 606/228; 606/230
[58] Field of Search ..................................... 528/170, 354, 528/327, 322, 355, 310, 361, 323; 525/417, 415, 411; 606/139, 228, 230

[56] References Cited

U.S. PATENT DOCUMENTS

| Re. 30,170 | 12/1979 | Goodman et al. | 528/327 |
|---|---|---|---|
| 2,386,454 | 10/1945 | Frosch | 260/78 |
| 4,226,243 | 10/1980 | Shalaby | 128/335.5 |
| 4,343,931 | 8/1982 | Barrows | 528/291 |
| 5,349,045 | 9/1994 | Jiang | 528/323 |
| 5,391,707 | 2/1995 | Jiang | 528/354 |
| 5,446,108 | 8/1995 | Jiang | 528/417 |
| 5,483,009 | 1/1996 | Jiang | 525/417 |

*Primary Examiner*—P. Hampton-Hightower

[57] ABSTRACT

Polyesteramides having amino acid-derived groups alternating with hydroxy acid-derived groups are useful in making shaped articles, particularly, shaped articles suitable for use as surgical devices.

24 Claims, No Drawings

POLYESTERAMIDES WITH AMINO ACID-DERIVED GROUPS ALTERNATING WITH ALPHA-HYDROXYACID-DERIVED GROUPS AND SURGICAL ARTICLES MADE THEREFROM

This Application claims benefit of Provisional Appln. 60/036,542, filed Jan. 28, 1997.

TECHNICAL FIELD

Polyesteramides with amino acid-derived groups alternating with alpha-hydroxy-derived groups and methods for their preparation are described herein. The polyesteramides are suitable for use in making shaped articles such as, for example, surgical devices.

BACKGROUND

Polyesteramides are polymers containing both ester linkages and amide linkages. Their significance for technology of surgical devices stems from the fact that the susceptibility of their ester linkages to hydrolysis confers upon them the ability to be eventually absorbed, or resorbed by a body into which they have been implanted and their amide linkages confer upon them the desirable mechanical properties characteristic of polyamides.

Fiber-forming polyesteramides obtained from the single stage reaction of approximately equimolar amounts of a monoalkanolamine and a dicarboxylic acid are known from U.S. Pat. No. 2,386,454. Polyesteramides indicated to be useful for the manufacture of absorbable sutures and other surgical devices are disclosed in U.S. Pat. No. 4,226,243 as obtained from the reaction of a bis-oxyamidodiol (itself derived from the reaction of diethyl oxalate with a monoalkanolamine such as ethanolamine) with a dicarboxylic acid ester. U.S. Pat. No. 4,343,931 discloses absorbable surgical devices manufactured from polyesteramides obtained by reacting a diamine with lactic or glycolic acid to produce a diamidediol, which is then reacted with a bischloroformate or a compound selected from the group consisting of dicarboxylic acids, diacidchlorides and dicarboxylic acid anhydrides.

Nylon refers to a family of high strength, resilient synthetic materials, the long chain molecules of which contain recurring amide groups. Articles fabricated from nylon have been widely accepted for a variety applications. Certain surgical applications, however, require a surgical device that is bioabsorbable. Nylon is not bioabsorbable and is therefore unacceptable in such circumstances.

It would be desirable to provide a surgical device that has strength and resiliency characteristics similar to those of nylon, but which is bioabsorbable.

SUMMARY

It has now been found that polyesteramides having amino acid-derived groups alternating with hydroxy acidderived groups are useful in making shaped articles, particularly, shaped articles suitable for use as surgical devices.

The polyesteramides are prepared from amino acids of the formula:

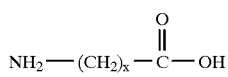

where x is an integer from 1 to 6; and alpha-hydroxy acids, such as, for example, glycolic acid.

The method of making the present polyesteramides involves blocking the amino group of the amino acid, reacting with an alpha-hydroxy acid, removing the blocking agent and then polymerizing to form the polyesteramide.

The resulting polyesteramide can be bioabsorbable and can be formed into shaped articles, for example by molding or extrusion. Particularly useful shaped articles include surgical devices such as sutures and other surgical implants.

DETAILED DESCRIPTION OF PREFERRED EMBODIMENTS

The polyesteramides described herein are of the following general formula:

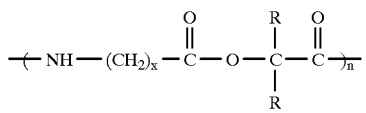

wherein x is an integer from 1 to 6 and R can be the same or different at each occurrence and is individually selected from the group consisting of hydrogen and $C_1$ to $C_4$ alkyl.

The polyesteramide is prepared from an amino acid of the formula:

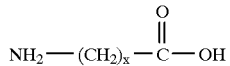

where x is an integer from 1 to 6. Preferred amino acids are those wherein x is 1 or wherein x is 5.

The first step in making the polyesteramide is to block the amino group of the amino acid. This will ensure that subsequent chlorination and reaction with the alpha-hydroxy acid occurs only at the acid group of the amino acid. Introduction of a blocking agent onto the amino group can be accomplished using any of the techniques known to those skilled in the art. Suitable blocking agents include benzyl chloroformate. Benzyl chloroformate can be reacted with the amino acid in the presence of a metal oxide (e.g., MgO) in an ice bath of an aqueous ether solution.

The protected amino acid is then converted to an acid halide. This can be achieved, for example, by ref luxing the protected amino acid with $SOX_2$ wherein X is F, Cl, Br or I in methylene chloride.

The blocked acid halide is reacted with an alpha-hydroxy acid. Suitable alpha-hydroxy acids include those of the formula:

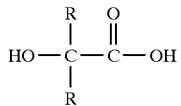

wherein R can be the same or different at each occurrence and is individually selected from the group consisting of hydrogen and $C_1$ to $C_4$ alkyl. Glycolic acid is the preferred alpha-hydroxy acid for making the polyesteramides described herein. The reaction of the acid chloride with the alpha-hydroxy acid can be carried out by refluxing in the presence of an inert diluent such as, for example, DMF and a tertiary amine, such as, for example, triethylamine (TEA).

The blocking agent is then removed from the acid chloride using techniques known to those skilled in the art. For example, if benzyl chloroformate is used as the blocking agent, the blocked acid chloride can be reacted with HBr in acetic acid to remove the blocking agent.

The resulting monomer which is recovered and purified has the general formula:

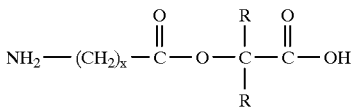

where x and R are as defined above.

The monomer should be purified, preferably to at least about 98 percent purity. The monomer may be purified using any known technique such as multiple distillations and/or recrystallizations.

The monomer is polymerized by heating to produce a self-condensation reaction. For example, melt polymerization of the monomer prepared from glycine and glycolic acid can be achieved by heating to around 240 degrees C.

If desired, any portion of the above-described amino acid/ester monomer employed in the polymerization reaction, e.g., from about 1 to about 99 mole percent can be replaced with a like mole percentage of another difunctional, self-condensing comonomer. Such monomers include compounds containing both an acid group and a second active group such as a hydroxy group, an amino group or a second acid group. Thus, by way of example, suitable comonomers include, hydroxycarboxylic acids, diacids and amino acids.

The polyesteramides can be formed into surgical articles using any know technique, such as, for example, extrusion, molding and/or solvent casting. The polyesteramides can be used alone, blended with other absorbable compositions, or in combination with nonabsorbable components. A wide variety of surgical articles can be manufactured from the polyesteramides described herein. These include but are not limited to clips and other fasteners, staples, sutures, pins, screws, prosthetic devices, wound dressings, drug delivery devices, anastomosis rings, and other implantable devices. Fibers made from the present polyesteramides can be knitted or woven with other fibers, either absorbable or nonabsorbable to form meshes or fabrics. Compositions including these polyesteramides can also be used as an absorbable coating for surgical devices.

Optional additives which may be present in compositions made from the polyesteramides described herein include plasticizers, release agents and other processing aids. Where the composition is used to make a surgical device, stearic acid or calcium stearate are particularly useful additives due to their biocompatiblity.

In another aspect, the compositions containing the polyester amides described herein can be used to make reinforced composites. Thus, for example, the polyesteramide composition can form the matrix of the composite and can be reinforced with bioabsorbable or nonabsorbable fibers or particles. Alternatively, a matrix of any bioabsorbable or non-bioabsorbable polymer composition can be reinforced with fibers or particulate material made from compositions containing the polyesteramides described herein.

In an alternative embodiment, the polyesteramides described herein are admixed with a filler. The filler can be in any particulate form, including granulate and staple fibers. While any known filler may be used, hydroxyapatite, tricalcium phosphate, bioglass or other bioceramics are the preferred fillers. Normally, from about 10 grams to about 400 grams of filler are mixed with 100 grams of polymer. The filled, cross-linked polymers are useful, for example, as a molding composition.

It is further contemplated that one or more medico-surgically useful substances can be incorporated into compositions containing the polyesteramides described herein. Examples of such medico-surgically useful substances include, for example, those which accelerate or beneficially modify the healing process when particles are applied to a surgical repair site. So, for example, articles made from compositions containing the present polyesteramides can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the articles, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye articles made from compositions containing the present polyesteramides in order to increase visibility of the article in the surgical field. Dyes, such as those known to be suitable for incorporation in sutures, can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, articles in accordance with this disclosure are dyed by adding up to about a few percent and preferably about 0.2% dye to the resin composition prior to extrusion.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. An esteramide compound having at least one unit of the general formula:

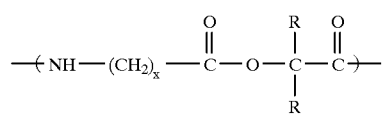

wherein x is an integer from 1 to 6 and R is the same or different at each occurrence and is individually selected from the group consisting of hydrogen and $C_1$ to $C_4$ alkyl.

2. An esteramide compound in accordance with claim 1 wherein x is 1 and R at each occurrence is hydrogen.

3. An esteramide compound in accordance with claim 1 wherein x is 5 and R at each occurrence is hydrogen.

4. An esteramide compound in accordance with claim 1 consisting essentially of repeating units of the general formula:

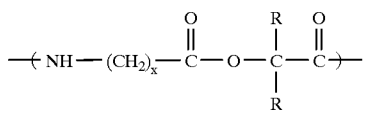

wherein x is an integer from 1 to 6 and R can be the same or different at each occurrence and is individually selected from the group consisting of hydrogen and $C_1$ to $C_4$ alkyl.

5. An esteramide compound in accordance with claim 4 wherein x is 1 and R at each occurrence is hydrogen.

6. An esteramide compound in accordance with claim 4 wherein x is 5 and R at each occurrence is hydrogen.

7. A method of making a polyesteramide comprising:
a) blocking the amino group of an amino acid;
b) halogenating the blocked amino acid to provide a chlorinated acid;
c) reacting the halogenated acid with an alpha-hydroxy acid to provide a monomer; and
d) de-blocking the product of step c);
e) polymerizing the monomer to produce a polyesteramide.

8. A method in accordance with claim 7 wherein step a) comprises blocking the amino group of an amino acid of the general formula:

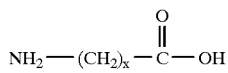

where x is an integer from 1 to 6.

9. A method in accordance with claim 7 wherein step a) comprises reacting an amino acid with benzyl chloroformate.

10. A method in accordance with claim 7 wherein step b) comprises reacting the blocked amino acid with a compound of the formula $SOX_2$ wherein X is selected from the group consisting of F, Cl, Br and I.

11. A method in accordance with claim 7 wherein step b) comprises chlorinating the blocked amino acid.

12. A method in accordance with claim 7 wherein step c) comprises reacting the acid halide with an alpha-hydroxy acid of the general formula:

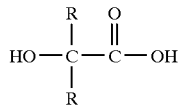

wherein R can be the same or different at each occurrence and is individually selected from the group consisting of hydrogen and $C_1$ to $C_4$ alkyl.

13. A method in accordance with claim 7 wherein step c) comprises reacting the acid halide with glycolic acid.

14. A method in accordance with claim 7 wherein the polyesteramide produced in step e) consists essentially of repeating units of the general formula:

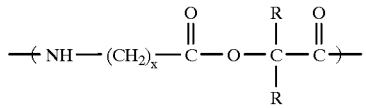

wherein x is an integer from 1 to 6 and R can be the same or different at each occurrence and is individually selected from the group consisting of hydrogen and $C_1$ to $C_4$ alkyl.

15. A composition comprising:
an esteramide compound having at least one unit of the general formula:

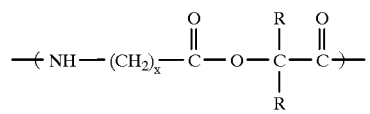

wherein x is an integer from 1 to 6 and R is the same or different at each occurrence and is individually selected from the group consisting of hydrogen and $C_1$ to $C_4$ alkyl.

16. A composition in accordance with claim 15 further comprising at least one medico-surgically useful compound.

17. A composition in accordance with claim 15 further comprising a plasticizer.

18. A composition in accordance with claim 15 further comprising a filler.

19. A composition in accordance with claim 15 further comprising one or more bioabsorbable polymer selected from the group consisting of homopolymers and copolymers of glycolide, lactide, trimethylene carbonate, dioxanone and caprolactone blended with the esteramide compound.

20. A composition in accordance with claim 15 wherein the esteramide compound consists essentially of repeating units of the general formula:

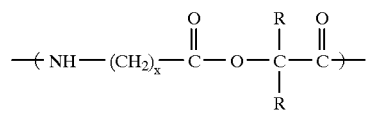

wherein x is an integer from 1 to 6 and R is the same or different at each occurrence and is individually selected from the group consisting of hydrogen and $C_1$ to $C_4$ alkyl.

21. A composition in accordance with claim 15 wherein the esteramide compound consists essentially of repeating units of the general formula:

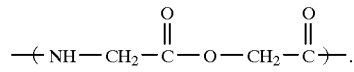

22. A composition in accordance with claim 15 wherein the esteramide compound consists essentially of repeating units of the general formula:

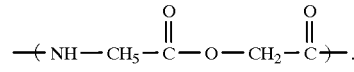

23. A surgical device comprising a shaped article made from the compound of any of claims 1 to 6.

24. A surgical device comprising a shaped article made from the composition of any of claims 15 to 21.

* * * * *